United States Patent

Wainwright

Patent Number: 5,370,128
Date of Patent: Dec. 6, 1994

[54] PAP BRUSH AND PAP UNIT CONTAINER SYSTEMS

[76] Inventor: Sharon R. Wainwright, 1072 Plymouth Ave., Elmira, N.Y. 14904

[21] Appl. No.: 160,665

[22] Filed: Dec. 2, 1993

[51] Int. Cl.$^5$ ............................................. A61B 10/00
[52] U.S. Cl. .................................................... 128/756
[58] Field of Search ............................... 128/756–759, 128/771; 604/317, 318, 322, 403

[56] References Cited

U.S. PATENT DOCUMENTS

| | | | |
|---|---|---|---|
| 3,888,126 | 6/1975 | Cross | 128/771 |
| 4,803,998 | 2/1989 | Kezes et al. | 128/759 |
| 4,857,042 | 8/1989 | Schneider | 604/317 |
| 5,131,402 | 7/1992 | Van Dooren | 128/757 |
| 5,184,626 | 2/1993 | Hicken | 128/756 |
| 5,191,899 | 3/1993 | Strickland et al. | 128/756 |

*Primary Examiner*—Max Hindenburg

[57] ABSTRACT

A new and improved pap brush and pap unit container system, for use in association with taking pap samples and preparing such samples for tests comprising a pap unit container having side walls and a bottom wall forming a well, a lid coupled with respect to the upper ends of the side walls to seal therein the fluid and brush containing the pap samples, a well located beneath the reservoir with a tube connecting the bottom of the reservoir with the well, the well having an opening therethrough for communication with exterior and a pop off cap removably positioned thereover; and a pap brush having an elongated handle and a bristle support member coupled thereto, a snap off coupling between the handle and the support member, a plurality of bristles extending parallel with the handle along the end of the support member remote from the handle, the bristles being in a linear configuration with the tips of the bristles forming an arcuate cross section with the longest bristles adjacent to the edges of the support member and the intermediate bristles tapering to the lowest bristles adjacent to the center of the support member, and spiral bristles extending upwardly from the center of the support member transverse to the axis of the handle for spiral type usage, the spiral type bristles being longest at the region adjacent the handle and shorter remote thereof.

5 Claims, 4 Drawing Sheets

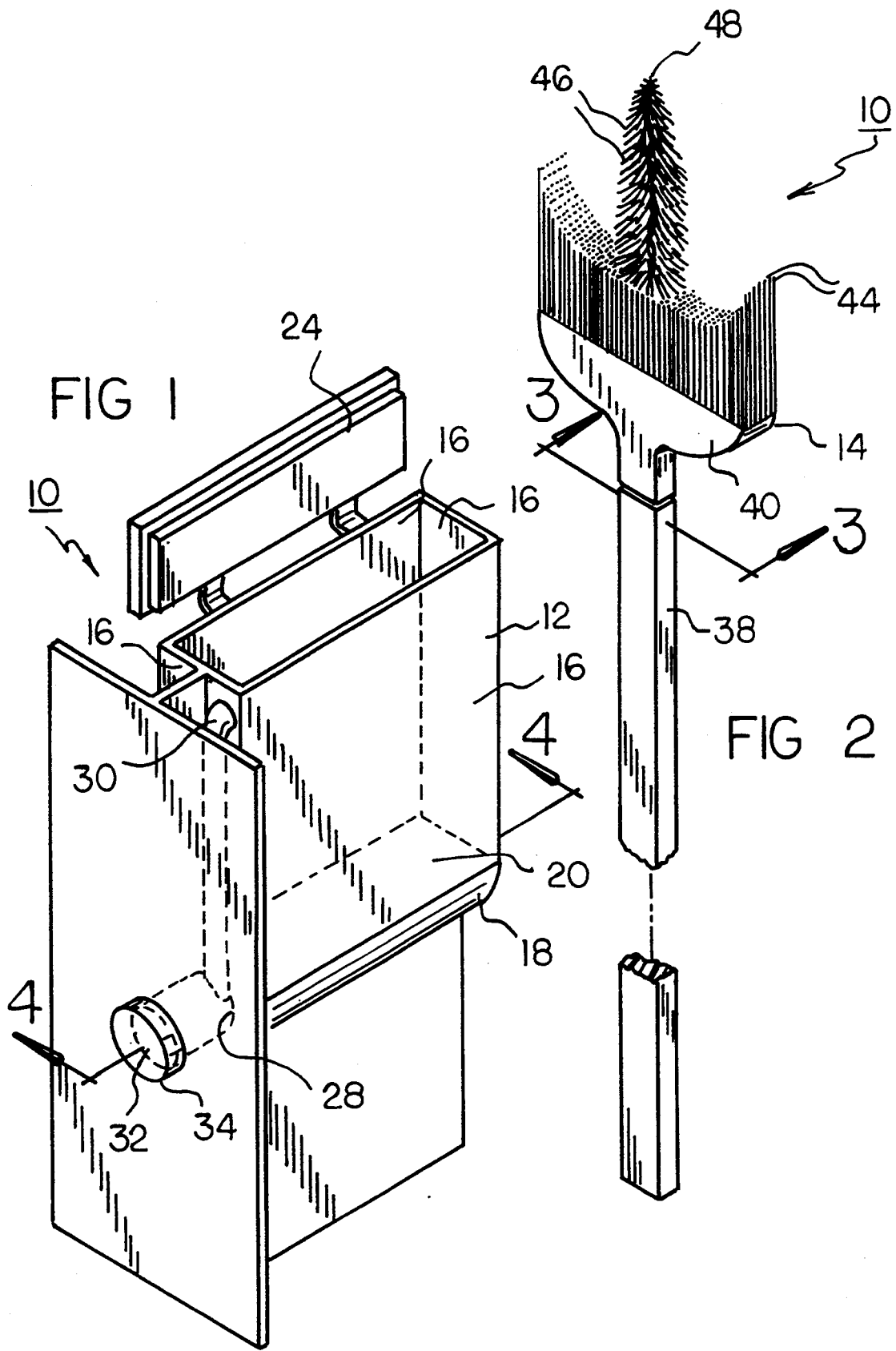

PAP BRUSH AND PAP UNIT CONTAINER SYSTEMS

BACKGROUND OF THE INVENTION

1. Field of the Invention

The present invention relates to pap brush and pap unit container systems and more particularly pertains to a pap brush and an associated container for facilitating pap testing.

2. Description of the Prior Art

The use of pap brushes and related devices is known in the prior art. More specifically, pap brushes and related devices heretofore devised and utilized for the purpose of taking pap samples are known to consist basically of familiar, expected and obvious structural configurations, notwithstanding the myriad of designs encompassed by the crowded prior art which have been developed for the fulfillment of countless objectives and requirements.

A wide variety of brushes and devices for use in the field of medicine are disclosed in the pad of literature. By way of example, U.S. Pat. Nos. 4,641,662 to Jaicks and 4,932,957 to Zwick disclose endocervical curette systems.

U.S. Pat. No. 4,757,826 to Abdulhay discloses an endocervical biopsy instrument.

U.S. Pat. Nos. 4,759,376 to Stormby and 5,022,408 to Mohajer disclose brushes for endocervical sampling.

In this respect, the pap brush and pap unit container systems according to the present invention substantially depart from the conventional concepts and designs of the prior art, and in so doing provide an apparatus primarily developed for the purpose of facilitating pap testing.

Therefore, it can be appreciated that there exists a continuing need for new and improved pap brush and pap unit container systems which can be used to facilitate pap testing. In this regard, the present invention substantially fulfills this need.

SUMMARY OF THE INVENTION

In view of the foregoing disadvantages inherent in the known types of pap brushes and related devices now present in the prior art, the present invention provides an improved pap brush and pap unit container system. As such, the general purpose of the present invention, which will be described subsequently in greater detail, is to provide a new and improved pap brush and pap unit container system apparatus and method which has all the advantages of the prior art pap brush and pap unit container system and none of the disadvantages.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved pap brush and pap unit container systems which have all the advantages of the prior art pap brushes and related devices and none of the disadvantages.

It is another object of the present invention to provide new and improved pap brush and pap unit container systems which may be easily and efficiently manufactured and marketed.

It is a further object of the present invention to provide new and improved pap brush and pap unit container systems which are of a durable and reliable construction.

An even further object of the present invention is to provide new and improved pap brush and pap unit container systems which are susceptible of a low cost of manufacture with regard to both materials and labor, and which accordingly is then susceptible of low prices of sale to the consuming public, thereby making such pap brush and pap unit container systems economically available to the buying public.

Still yet another object of the present invention is to provide new and improved pap brush and pap unit container systems which provide in the apparatuses and methods of the prior art some of the advantages thereof, while simultaneously overcoming some of the disadvantages normally associated therewith.

Still another object of the present invention is to acquire pap samples more efficiently and economically.

Yet another object of the present invention is to handle pap samples more efficiently and economically.

Even still another object of the present invention is to provide a new and improved pap brush and pap unit container system, for use in association with taking pap samples and preparing such samples for tests comprising, in combination a pap unit container having side walls and a bottom wall forming a well for the retention of fluid for intermixing with pap samples to be tested, a lid coupled with respect to the upper ends of the side walls to seal therein the fluid and brush containing the pap samples, a well located beneath the reservoir with a tube connecting the bottom of the reservoir with the well, the well having an opening therethrough for communication with exterior and a pop off cap removably positioned thereover; and a pap brush having an elongated handle and a bristle support member coupled thereto, a snap off coupling between the handle and the support member to allow for the separation thereof and the placing of the support member into the reservoir, a plurality of bristles extending parallel with the handle along the end of the support member remote from the handle, the bristles being in a linear configuration with the tips of the bristles forming an arcuate cross section with the longest bristles adjacent to the edges of the support member and the intermediate bristles tapering to the lowest bristles adjacent to the center of the support member, and spiral bristles extending upwardly from the center of the support member transverse to the axis of the handle for spiral type usage, the spiral type bristles being longest at the region adjacent the handle and shorter remote thereof.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a pap unit container, part of the pap brush and pap unit container system, constructed in accordance with the principles of the present invention.

FIG. 2 is a perspective view of a pap brush, part of the pap brush and pap unit container system, constructed in accordance with the principles of the present invention.

DESCRIPTION OF THE PREFERRED EMBODIMENT

Figure 3:
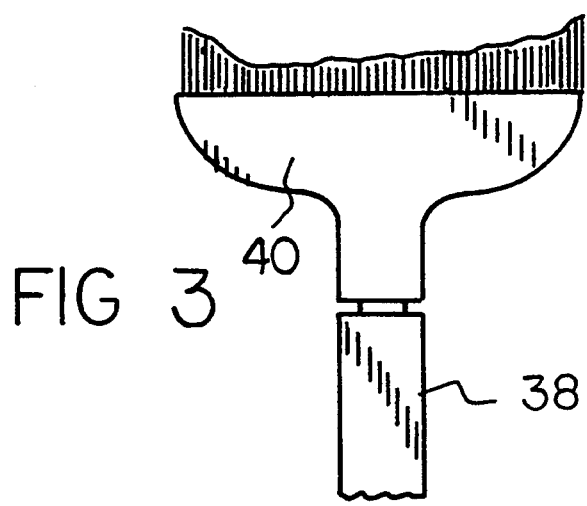
FIG. 3 is an end view of a portion of the brush of FIG. 2 taken along line 3—3 of FIG. 2.
Figure 4:
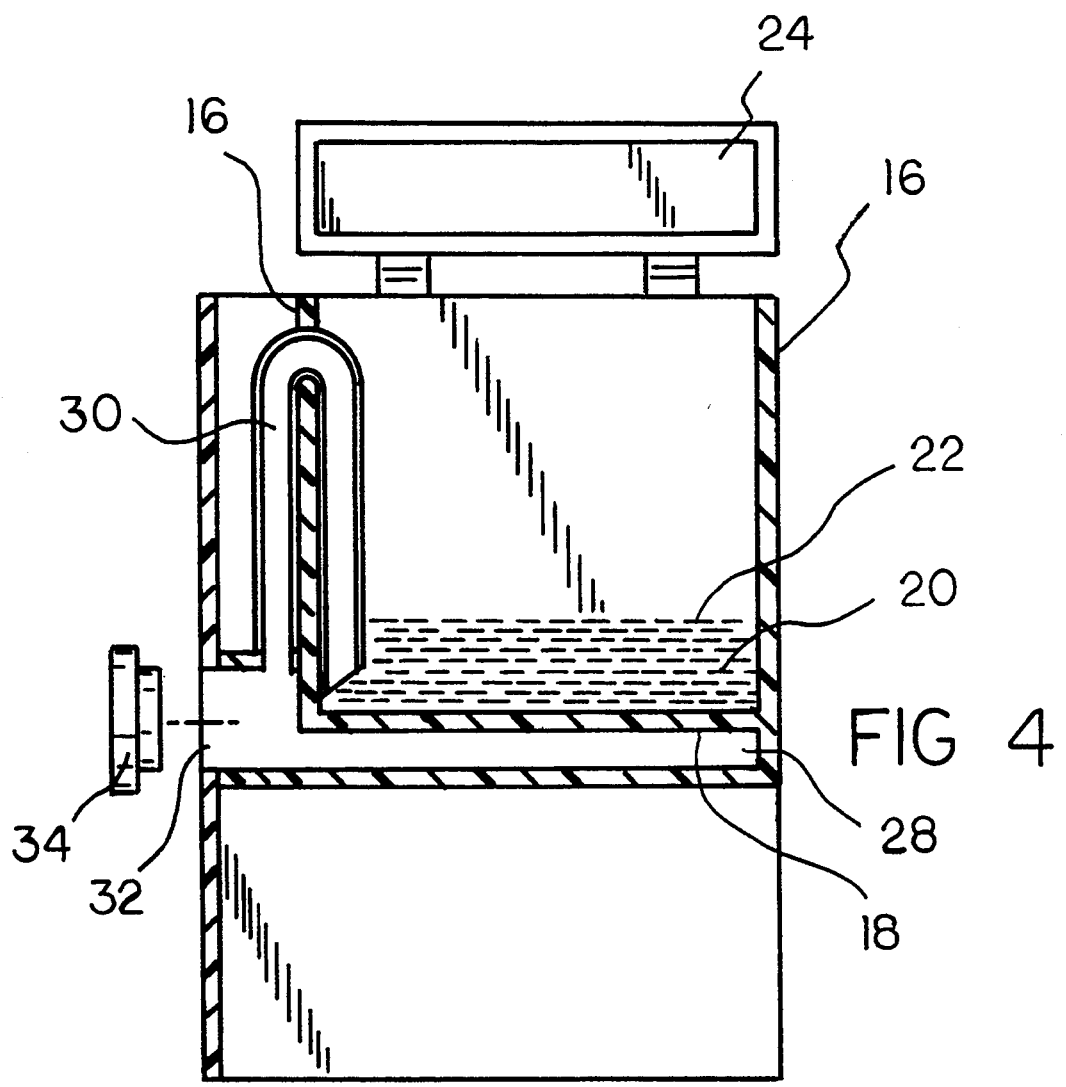
FIG. 4 is a sectional view of the pap unit container taken along line 4—4 of FIG. 1.

With reference now to the drawings, and in particular to FIG. 1 thereof, a new and improved pap brush and pap unit container system embodying the principles and concepts of the present invention and generally designated by the reference numeral 10 will be described.

More specifically, it will be noted in FIGS. 1 through 4 that system 10 of the present invention includes, in its broadest context, a container 12 and a brush 14. Together, the pap brush 14 and pap unit container 12 are adapted for use in association with taking pap samples and preparing such samples for tests.

More specifically, the pap unit container 12 is formed of side walls 18 and a bottom wall 18. Together a reservoir 20 is formed in the bottom of the container 12. Such reservoir 20 is for the retention of fluid 22 for intermixing with pap samples to be tested. A lid 24 is coupled with respect to the upper ends of the side walls to seal therein the fluid and brush portion containing the pap samples.

Located beneath the fluid in the reservoir is a well 28. A tube 30 connects the bottom of the reservoir with the well. The well has an opening 32 therethrough for communication with exterior. Lastly, a pop off cap 34 is removably positioned over the opening for pouring out the mixed fluid and sample from the container for testing. Vertically extending plates extend along one side of the container and from the bottom of the well to provide, at their lower ends, a surface upon which the container may stand.

The second component is the pap brush 14. The pap brush 14 has an elongated handle 38. At the end of the handle is a bristle support member 40 attached thereto. A snap off coupling 42 is located between the handle 38 and the support member. This is to allow for separation thereof. After the separation, the support member is placed with its bristles into the reservoir. The side plates of the support member remote from the handle is formed with bristles. A first plurality of bristles 44 extend parallel with the axis of the handle 38 along the remote side 46 of the support member 40. The bristles are perpendicularly extended from the end of the support member remote from the handle and oriented in a linear fashion with their tips in an arcuate shape with the longest bristles adjacent to the edges of the support member and the bristles gradually tapering to the shortest bristles adjacent to the axis of the handle. Supplemental bristles 46 extend radially outwardly from a shaft 48 which extends coaxially with the handle from the support member. The supplemental bristles are for spiral type usage. Such spiral type bristles 46 are longest at the region adjacent the support member and shortest remotely therefrom.

Figure 5:
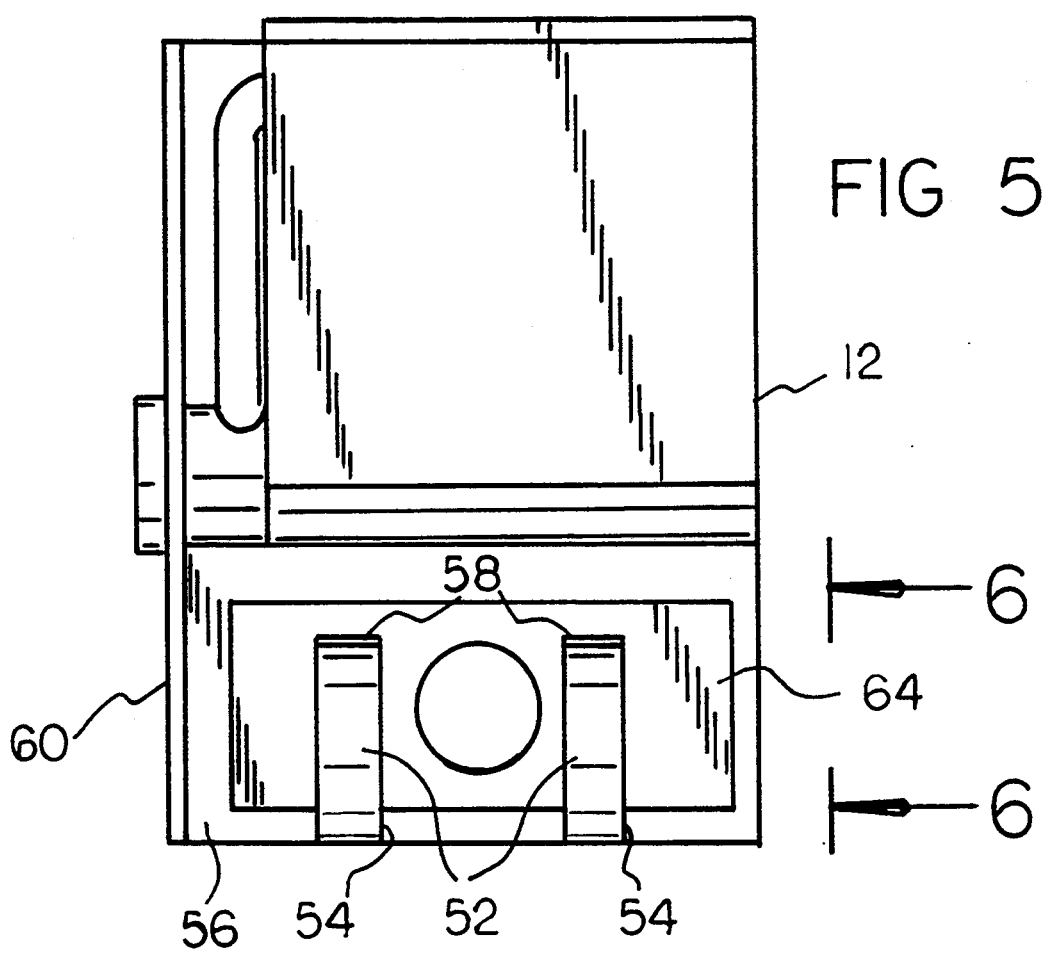
FIG. 5 is a rear elevational view of the pap unit container but constructed in accordance with an alternate embodiment of the present invention.
Figure 6:
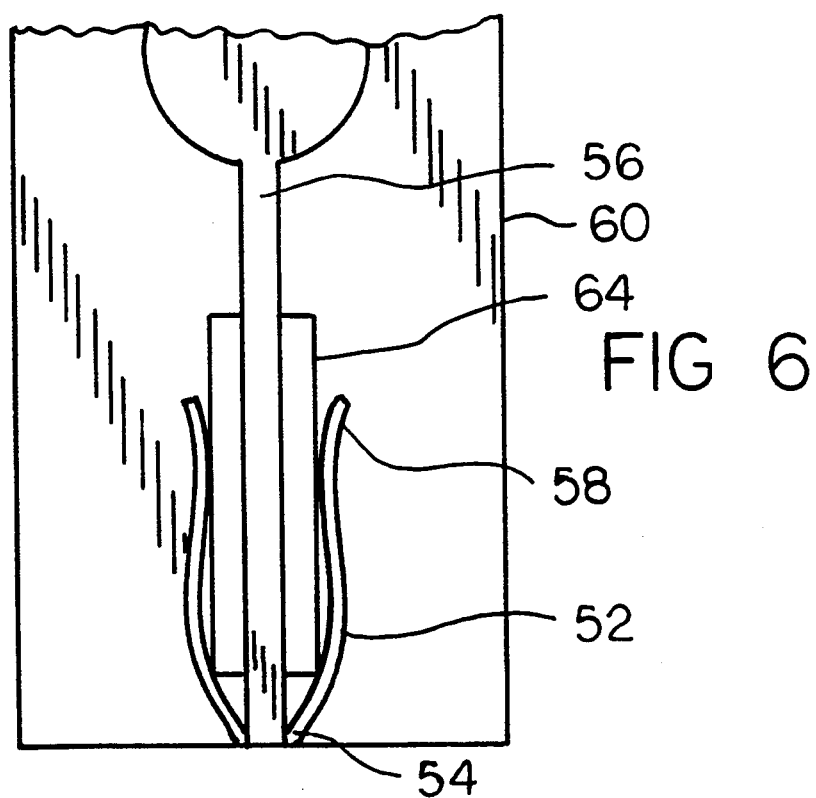
FIG. 6 is an end view of the pap unit container taken along 6—6 of FIG. 5.

An alternate embodiment of the invention may be seen in FIGS. 5 and 6. Such alternate embodiment includes all of the components of the prior embodiment but further includes clips 52. The lower ends 54 of the clips 52, are secured on opposite sides of the vertical support plate 56. The upper ends 58 are spring urged towards each other. One side of plate 56 is coupled to an associated support plate 60 to provide support surfaces therebeneath. Transparent slide holders 64 may thus be removably held to support plate 56 for convenience to a user. Such holders are for receiving and supporting specimens.

Figure 7:
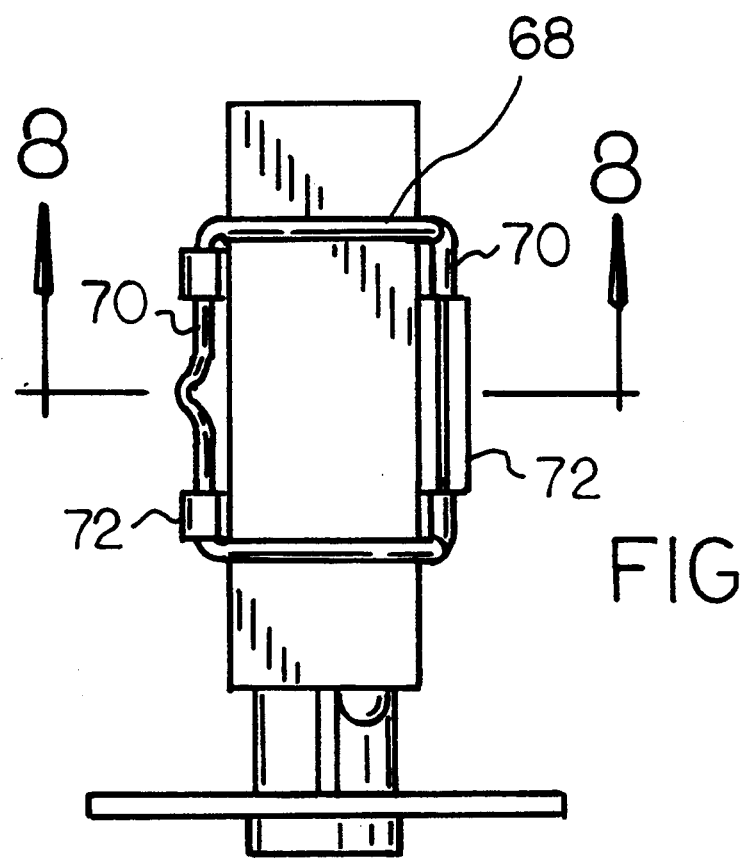
FIG. 7 is a planned view of a pap unit container constructed in accordance with another alternate embodiment of the invention.
Figure 8:
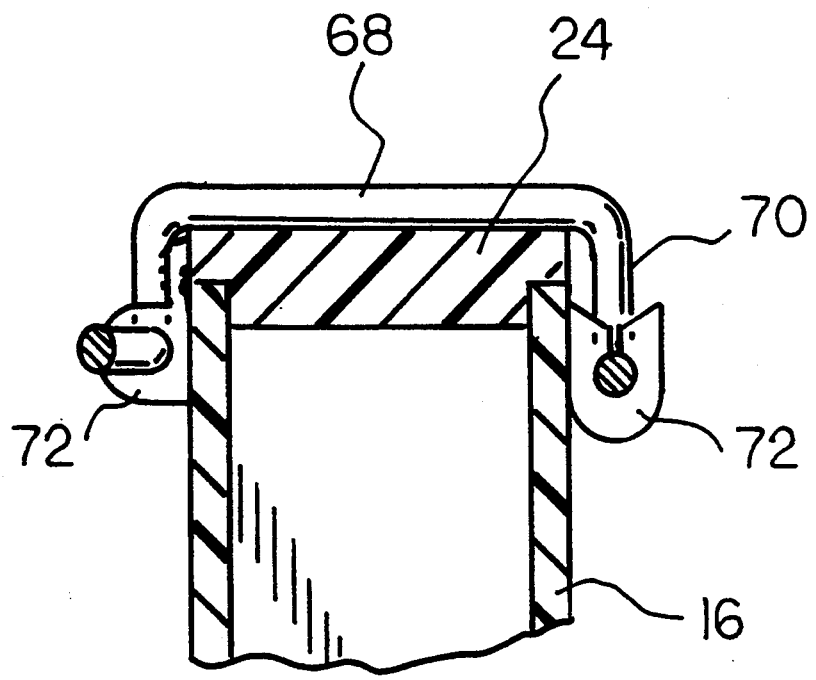
FIG. 8 is a sectional view taken along line 8—8 of FIG. 7.

The third and final alternate embodiment of the invention is shown in FIGS. 7 and 8. The apparatus of this embodiment further includes a locking band 68. Such band is in the form of a rectangularly configured wire positionable over the lid 24 of the container 12. Parallel sides 70 extend downwardly and are secured in supports 72. When so coupled, the lid may be removed only after cutting the wire. Tampering with the contents is thus abated since it requires cutting of the band.

There is currently a shortage of trained cytologists in this country to analyze pap smears. There is also a crisis in health care due to rising costs on everything, including laboratory fees and supplies. In addition, there is an environmental crisis due to huge amounts of medical waste that must be disposed of. The Pap Brush and Unit is a two-part device, designed to make taking pap smears easier, faster, safer, and more accurate, and reduce the cost of taking and analyzing the specimens.

The first part is a brush with two sets of bristles that enables a doctor or nurse practitioner to take endocervical and ectocervical cell samples at the same time. The brush is inserted into the endocervical canal and turned 180 degrees to extract a cell sample. With the current method, these two types of samples are taken separately with a cotton swab, a wooden scraper, or with two separate brushes.

The Pap Brush and Unit has a six inch plastic handle with a 1 inch by 1.25 inch nylon brush on the end. The brush includes wide bristles as well as long center bristles and resembles a butter brush with a small pipe cleaner in its center.

It is this double-brush design that enables the medical professional to take both samples at the same time. The double-brush enables the medical person to take cells from the entire surface of the cervix, providing a better sample for the cytologists who will analyze the sample.

In addition, the Pap Brush and Unit saves money in two ways. First, since it combines both tests with a single device, less brushes are required. This cuts down on resources, medical waste, and medical costs. Secondly, the sample is all on one slide, enabling the cytologist to screen the specimen in one step. This is especially important because there is such a shortage of cytologists. This will also reduce the amount of billable time spent on each specimen, thereby cutting down on the cost of processing the test and reducing the cost of health care for everyone.

After the cell sample is taken with the brush, the medical professional can either smear the brush directly onto a glass slide or snap off the brush head and place it into the second part of the Pap Brush and Unit, a unit for carrying the pap smear.

The second part of the Pap Brush and Unit provides a means of transporting the specimen safely to the lab. It is a small container 1⅜ inches high with a snap-on lid (1¼ inches by ⅜ of an inch). Inside the container is 2 CCs of cytofixative to preserve the specimen. There is a ¼ inch pop-off cap on the side, so that the specimen can be squeezed out onto a slide.

In the lab, the specimen is labeled and processed inside the carrying unit, enabling the cytologist to examine the specimen without ever having to touch the unit. This reduces the risk of contamination by lab personnel or, conversely, contamination of the lab personnel from the specimen.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved pap brush and pap unit container system, for use in association with taking pap samples and preparing such samples for tests comprising, in combination:

a pap unit container having side walls and a bottom wall forming a well for the retention of fluid for intermixing with pap samples to be tested, a lid coupled with respect to the upper ends of the side walls to seal therein the fluid and brush containing the pap samples, a well located beneath the reservoir with a tube connecting the bottom of the reservoir with the well, the well having an opening therethrough for communication with exterior and a pop off cap removably positioned thereover; and a pap brush having an elongated handle and a bristle support member coupled thereto, a snap off coupling between the handle and the support member to allow for the separation thereof and the placing of the support member into the reservoir, a plurality of bristles extending parallel with the handle along the end of the support member remote from the handle, the bristles being in a linear configuration with the tips of the bristles forming an arcuate cross section with the longest bristles adjacent to the edges of the support member and the intermediate bristles tapering to the lowest bristles adjacent to the center of the support member, and spiral bristles extending upwardly from the center of the support member transverse to the axis of the handle for spiral type usage, the spiral type bristles being longest at the region adjacent the handle and shorter remote thereof.

2. For use in association with taking pap samples and preparing such samples for tests, an improved pap brush and pap unit container system comprising:

a pap unit container having side walls and a bottom wall forming a well for the retention of fluid for intermixing with pap samples to be tested, a lid coupled with respect to the upper ends of the side walls to seal therein the fluid and brush containing the pap samples, a well located beneath the reservoir with a tube connecting the bottom of the reservoir with the well, the well having an opening therethrough for communication with exterior and a pop off cap removably positioned thereover.

3. The apparatus as set forth in claim 2 and further including clips coupled to the pap unit container for supporting transparent holders for receiving and supporting specimens.

4. The apparatus as set forth in claim 2 and further including a locking band positionable over the top of the container and lid for securing the lid in the closed position whereby tampering with the contents of the container will require the cutting of the band.

5. For use in association with taking pap samples and preparing such samples for tests, an improved pap brush and pap unit container system comprising:

a pap brush having an elongated handle and a bristle support member coupled thereto, a snap off coupling between the handle and the support member to allow for the separation thereof and the placing of the support member into the reservoir, a plurality of bristles extending parallel with the handle along the end of the support member remote from the handle, the bristles being in linear configuration and perpendicularly extended from the end of the support member remote from the handle with the tips of the bristles forming an arcuate cross section with the longest bristles adjacent to the edges of the support member and the intermediate bristles tapering to the lowest bristles adjacent to the center of the support member, and the spiral bristles extending upwardly from the center of the support member transverse to the axis of the handle for spiral type usage, the spiral type bristles being longest at the region adjacent to the handle and shorter remote thereof.

* * * * *